United States Patent [19]

Smith

[11] Patent Number: 5,520,918
[45] Date of Patent: May 28, 1996

[54] LOW IRRITANT SKIN-COSMETIC COMPOSITION FOR DAILY TOPICAL USE, ITS APPLICATION AND MANUFACTURE

[75] Inventor: Walter P. Smith, New Canaan, Conn.

[73] Assignee: Mary Kay Cosmetics, Inc., Dallas, Tex.

[21] Appl. No.: 214,032

[22] Filed: Mar. 15, 1994

Related U.S. Application Data

[63] Continuation-in-part of Ser. No. 944,503, Sep. 14, 1992, abandoned.

[51] Int. Cl.$^6$ .................................. A61K 7/00; A61K 7/06
[52] U.S. Cl. ........................ 424/401; 424/70.1; 514/847; 514/880
[58] Field of Search ........................... 424/40, 195.1, 424/401, 70.1; 514/880, 847

[56] References Cited

U.S. PATENT DOCUMENTS

| | | | |
|---|---|---|---|
| 4,294,852 | 10/1981 | Wildnauer | 424/317 |
| 4,608,370 | 8/1986 | Aronsohn | 514/864 |
| 4,699,924 | 10/1987 | Durrant | 514/738 |
| 5,091,171 | 2/1992 | Yu | 424/642 |
| 5,156,836 | 10/1992 | Uchikawa | 424/70 |
| 5,185,325 | 2/1993 | Brawn | 514/880 |

FOREIGN PATENT DOCUMENTS

WO9310756  6/1993  WIPO.

*Primary Examiner*—Thurman K. Page
*Assistant Examiner*—Sally Gardner
*Attorney, Agent, or Firm*—Handal & Morofsky

[57] ABSTRACT

A skin-conditioning composition is disclosed which can be applied topically to improve skin cell renewal rates with low irritation levels and comprises minor proportions of a salicylic acid and a somewhat hydrophobic alpha hydroxy aliphatic acid formulated into an acidic cosmetic composition, optionally with an anti-irritant or anti-oxidant additive. Preferred acids are salicylic and lactic and appropriate compositions are also useful topical treatments for the scalp to reduce hair loss.

9 Claims, No Drawings

LOW IRRITANT SKIN-COSMETIC COMPOSITION FOR DAILY TOPICAL USE, ITS APPLICATION AND MANUFACTURE

This application is a continuation-in-part of application Ser. No. 07/944,503, filed 14 Sep. 1992, now abandoned.

TECHNICAL FIELD

This invention relates to a novel skin-conditioning composition and its method of application or use, and to its manufacture. More particularly, it relates to a cosmetic composition which can improve the appearance and condition of the skin. In a further embodiment, the invention relates to a novel cosmetic composition specifically suited for application to the skin of the scalp and which is effective in improving the condition of the hair. The invention further relates to a method of application of this novel scalp-conditioning composition and to its use in improving hair condition.

BACKGROUND

As is well known, and the subject of ordinary biology text books, the skin is a complex system with protective epidermal layers, growing endodermal layers, often a keratinous outer layer, systems of glands and follicles and systems for the supply of intracellular and extracellular fluids. Active methods and compositions for treating the skin which do more than provide a passive coating on it, must take account of its complexity.

Many cosmetic formulations are known for skin treatment that show beneficial effects in improving skin appearance and which work by promoting skin renewal. Renewal is stimulated as a natural process by removal of the outer keratinous layer of the skin system. Such removal can be effected mechanically, for example by abrasive means, or chemically by agents promoting skin system imbalances or destruction of one or more layers of the skin system. Such substances are often described as exfoliants.

EP 0 336 812 published Nov. 10, 1989, discloses the use of a combination of a pyrimidine derivative with a salicylic acid derivative to stimulate hair growth and reduce hair loss. A preferred pyrimidine is minoxidil. The examples disclose n-octanoyl- 5 salicylic acid or n-decanoyl-5 salicylic acid used in combination with minoxidil. Minoxidil is an expensive prescription product. As is acknowledged in EP 0 336 812, page 2, line 26 salicylic acids are known to have keratolytic activity, but they are also irritants. The preferred salicylic acids disclosed in the Examples have carbonyl moieties in the 5 position through which a substantial alkyl group is coupled. Similar salicylic acids with a chain of at least three carbon atoms coupled at the five position through a carbonyl group are disclosed in EP 0 378 936 for the treatment of aging of the skin.

EP 0423 929 discloses the use of a class of lactic acid compounds including lactic acid and salts thereof as skin-whitening agents.

EP 0 273 202 published Jun. 7, 1988 contains a broad spectrum disclosure of the use of wide ranges of hydroxy acids as additives to enhance the topical actions of cosmetic and therapeutic agents by enhancing skin penetration and efficacy. Several classes of hydroxy acids are disclosed in EP 0 273 202 A2 for use as additives, namely hydroxymonocarboxylic acids, hydroxydicarboxylic acids and an extensive third class which is a miscellaneous recitation of hydroxycarboxylic acids including acids with cyclic moieties. This class is exemplified by a list of some twenty or thirty compounds. Free acid, lactone and salt forms of the acid are included. 2-hydroxypropanoic acid, lactic acid, is recited, as one acid amongst many, in three and one half pages of disclosure relating to the acid additive to be used in the invention. Examples 3, 6, 8, 15, 19 and 26 of 29 Examples employ lactic acid to enhance the penetration and efficacy of minoxidil, thionicotinamide, clotrimazole, dipyridamole, octyl dimethyl PABA with dioxybenzone and hydroquinone.

At p.2, lines 35 et seq. EPA provides a very general listing of categories of cosmetic and pharmaceutical agents that is enhanced by these additives. These categories are given by way of examples of any natural or synthetic substances intended for topical application to the skin of humans or animals. Such natural and synthetic substances make up the wide field of application of the invention of this prior publication. Substances whose activity is purportedly enhanced by the invention of the EPA include anesthetics, softeners, foot care agents vitamins, tanning agents and the like. Clearly any topically useful substance is intended to be included. Claim 3 of the publication recites salicylic acid among some fifty or sixty or more specific cosmetic or pharmaceutical agents that are subjects of the application, but there appear to be no examples or test data to show what effect, if any, one of the three classes of hydroxy acid of the EPA invention has on the activity of salicylic acid.

Some comparative test data, page 16, apparently show enhancement of the activity of thio- and 6-aminonicotinamides by lactic acid, but there is no differentiation between the effects of various hydroxy acids.

In its preferred embodiments, the present invention provides what are colloquially known as anti-aging formulations and hair-loss remedies having advantages aver the prior art formulations available heretofore.

It is one object of the invention to provide a skin-conditioning composition which can improve the appearance of skin without inducing excessive irritation.

Another object of the invention is to provide a skin-conditioning composition which will promote, stimulate or accelerate skin renewal, again with tolerable or reduced irritation levels.

It is a further object of the invention to provide such a formulation which is a non-prescription product suitable for direct over-the-counter sales to consumers.

A still further object is to provide such a skin-conditioning composition in a dermatological formulation suitable for professional use.

Yet another object of the invention is to provide a skin-conditioning composition for use on the scalp that can improve hair condition and is suitable for direct over-the-counter sales to consumers, for use without professional supervision.

SUMMARY OF THE INVENTION

The invention, as claimed, is intended to provide a remedy. It solves the problem of providing a cosmetic or therapeutic composition which is effective in improving skin condition without incurring an unacceptable level of irritation. The invention solves the further problem of providing a skin conditioning composition which better stimulates skin renewal at moderate irritation levels, than has heretofore been possible.

To solve this and other problems the invention provides a novel skin conditioner having a combination of active ingredients namely an alpha hydroxy acid, especially a lower-alkyl alpha hydroxy carboxylic acid, and a salicylic acid in effective proportions. As a result of laboratory research and clinical trials, which included comparative tests of efficacy and side effects, I have surprisingly discovered a synergistic effect yielding an improved combination of skin-conditioning properties when an alpha hydroxy acid is used as a major active ingredient together with a minor amount of a salicylic acid. These two acids, or mixtures with or of their derivatives can be formulated as active ingredients, up to about 10 percent each by weight of the composition, in a wide range of cosmetics compositions, including tonics, creams and lotions.

Data obtained as a result of the research and trials I have conducted or commissioned, show a high level of stimulation of skin renewal, as witnessed by a simple cell renewal assay, coupled with a low level of irritation as indicated by a standard clinical test. The combined levels of stimulation and low irritation are not obtained when the active ingredients are used individually even if a variety of concentrations is tried.

Additional data show a novel and useful combination of properties for conditioning the scalp, a particular area of the skin, which suggest that the compositions of this invention are effective in treating hair loss.

Further data show an increased efficacy of the active ingredients is obtainable by incorporating an antioxidant or anti-inflammatory in the composition.

In another aspect of the invention I have discovered that skin-treatment compositions having a surprisingly improved efficacy as low irritant, skin cell renewal stimulants, when used over a period of weeks, can be formulated by using as essential active acidic ingredients a major proportion of lactic acid, or other water soluble alphahydroxy acid, as described herein, having a water solubility of at least 1 g. in 3 ml. at 25° C. together with a minor proportion of a cosmetically compatible acid of moderate oil solubility (especially solubility in a low polarity organic solvent) for example, a solubility of at least 1 g. per 250 ml. in ether or at least 1 g. per 100 ml. of a triglyceride or fatty acid based oil is acceptable. Such acid typically has only moderate water solubility, for example, less than about 1 g. in 5 ml. at 25° C. Generally, acids with a molecular weight below about 400, or more preferably, below 250 can be used, with hydroxy acids and betahydroxy acids such as a salicylic being more preferred.

Whereas lactic acid is readily soluble in water, other low-molecular weight carboxylic acids such as salicylic, mandelic, and racemic tartaric acid, are only moderately or sparingly water soluble.

In general, low water solubility of carboxylic acid correlates with a substantial oil solubility. Desirable is significant solubility in a lipid similar to the lipid compounds of the skin. While not being bound by any particular theory, my results suggest that a somewhat lipid soluble fatty acid may enter the lipid phase of the skin system and provide a longer term, slow release skin acidifying effect.

I have found that using these acids in combination with lactic acid produces significant improvements in skin cell renewal stimulation in relation to irritancy, as shown by the results of experiments I have conducted, data from which are reported hereinbelow.

In a preferred embodiment, the invention provides a low-irritant, skin conditioning composition suitable for topical application to the skin comprising:

a) from about 0.05 to 10 percent of a salicylic acid or acids;

b) from about 0.1 to 20 percent of a hydrophilic lower-alkyl alpha hydroxy carboxylic acid or acids having from 3 to 10 carbon atoms; and c) a cosmetically compatible aqueous solvent system for both a) and b);

wherein said salicylic acid and said hydroxy carboxylic acid together comprise from about 0.15 to 30 percent of the composition wherein further said composition has an acidic pH of from about 2 to 5.5, said percentages being based on the weight of the composition. The acidic pH ensures inter alia that both acid ingredients will be partially or wholly in the free acid form even if introduced into the composition in a salt form.

In the best known embodiment of the invention a) is salicylic acid and b) is lactic acid, and the two are present in a weight proportion that is close to about 1:2. Also, the best known embodiment of the invention is a skin-conditioning composition with a pH of about 5 or a little less, in which the salicylic and lactic acids will both normally be in a free acid form.

In other aspects, the invention provides a scalp-conditioning formulation with similar active ingredients to the foregoing. It also provides methods of use of the inventive compositions, methods of application to the skin and scalp, and hence to the hair, and methods of manufacturing the novel compositions.

BEST MODE FOR CARRYING OUT THE INVENTION

My research has shown that when two well known cosmetic ingredients, a salicylic acid and a lactic-like alpha hydroxy carboxylic acid are combined in a skin-conditioning composition, in modest concentrations, at a rather acid pH, with a moderate excess of lactic acid over salicylic acid, the resultant inventive skin-conditioning composition is very effective in stimulating skin renewal, and thence improving the skin's condition and appearance while causing only low levels of irritation at effective dosages.

My invention is intended to provide a cosmetically acceptable composition of substantial acidity which can be applied to the skin as an exfoliant, will stimulate skin renewal, and yet does not burn the skin or induce such irritation as to render its use impractical or ineffective. Preferred embodiments of my invention are formulated to be keratolytic without inducing an excessive immune response.

Additional research has shown that growth-related characteristics of hair were improved when my inventive skin-conditioning composition was applied to the scalp.

I have also been able to demonstrate, with comparative test data, that the efficacy of a skin exfoliant composition, including the inventive skin-conditioning composition described herein, can be improved by incorporating significant quantities of one or more antioxidants or anti-inflammatory agents in the conditioner. Common physiologically acceptable and cosmetically compatible antioxidants are vitamins C and E. Apparently, such antioxidants function as anti-irritants, increasing the effective dose any particular individual can tolerate. Other anti-irritants, anti-inflammatory agents and anti-oxidants can be used.

My discovery is notable and has potential wide applicability because the active ingredients are well-adapted for consumer use, without professional supervision. The conditions and concentrations required for useful results are moderate and innocuous and the active ingredients can readily be incorporated in a wide range of conventional cosmetic compositions, such as tonics, creams, lotions, gels, sticks or salves, without difficulty.

Salicylic acid and lactic acid each have a long history of use as cosmetics and in medications. They are known to be safe when absorbed and substantially free of harmful side effects, even when used over repeatedly for long periods of time. Lactic acid is a naturally occurring biological present in the blood and muscle fluid of man and other animals. Lactic acid has been used for many years in cosmetics as a moisturizing factor.

Salicylic acid is also a natural biological, found in plants, and is an FDA approved over-the-counter drug for anti-acne and anti-dandruff treatments. Such treatments involve the application of cosmetic or medicament formulations to the skin, including the scalp, and have, with extensive use over many years, been thoroughly tested for side effects. Being also economical, and soluble in cosmetically desirable hydroalcoholic carrier vehicles, salicylic and lactic acid are ideally suited to the purposes of the present invention.

The effects I have observed are obtainable not only with the precise ingredients, proportions and conditions used to generate the test data described herein, but at least to some useful degree, can also be obtained with some variations of the preferred ingredients, proportions and conditions. Based upon the data disclosed hereinbelow, those of ordinary skill in the art will wish to try alternative analogous ingredients, proportions and conditions while still obtaining some of the benefits provided by the effects I have discovered.

Some such possible analogous ingredients, proportions and conditions will now be described. Unless otherwise specified, either explicitly, or by the context, the percentages disclosed herein are weight percent based on the weight of the skin-conditioning composition.

Active ingredient a): a salicylic acid

Preferably, the salicylic acid of my inventive composition is selected from the group consisting of salicylic acid and analogs and esters thereof. Preferably, said analogs including one or more substituents in the 3, 4, 5, or 6 position, which substituents have not more than six carbon atoms in total and include substituents with acidic or polar character. However, any substituents in the salicylic acid ring should preferably include a hydrocarbon moiety as the first moiety adjacent the ring. Preferably, said esters are esters of saturated or unsaturated aliphatic acids having from 1 to 15 carbon atoms, in addition to their hydroxyl, and are coupled to the aromatic hydroxyl, leaving the aromatic carboxyl free.

Salicylic acid is 2-hydroxybenzoic acid having a —COOH carboxyl group attached to a first carbon atom of the benzene ring and having a hydroxyl group at the adjacent or ortho carbon. Clearly, this structure is capable of a great range of substituents at positions other than the 1 and 2 positions occupied by the characteristic carboxyl and hydroxyl moieties, while still retaining the desirable characteristics of acidity, hydroalcoholic solubility and cosmetic compatibility. The latter characteristic implies that the substituted salicylic acid should be non-toxic and stable, should have the physical or physico-chemical ability to be satisfactorily incorporated in conventional cosmetic formulations and should be aesthetically appealing or acceptable with regard to odor, skin feel and color. Mixtures of salicylic acids can also be used.

Possible substituents of salicylic acid will mostly be directed to the 4 or 5 position by the presence of the polar carboxyl and hydroxyl substituents in the 1 and 2 positions. A limit of six carbon atoms as a total for all the substituents is a number within which the requirements described above can reasonably be expected to be satisfied. More hydrogenated carbon atoms would render the salicylic acid unduly hydrophobic and inadequately soluble in a hydroalcoholic vehicle. However, the inclusion of non-basic polar moieties of modest reactivity, such as hydroxyl, keto, aldehyde, or lower ester among said substituents, will counteract such poor hydroalcoholic solubility and substituents with such moieties may have ten or more carbon atoms in total. Thus, a 4- or 5-position substituent may also comprise a linear or branched alkyl or alkoxy group having from 1 to 18 carbon atoms. Preferably, the salicylic acid is free of basic groups, such as basic nitrogenous moieties, which would interfere with the desired acidity of the composition. Halo substituents, other than chloro are generally not desirable, and chloro substituents are possible, but not preferred. In selecting an alternative to salicylic acid, factors to consider in addition to acidity and some hydrophilicity, are irritation potential, ability to penetrate into the skin and material cost.

Clearly, any compound which employs an aryl moiety substituted at adjacent positions with a carboxyl and a hydroxyl group, which meets the criteria described above and which demonstrates the efficacy described herein, to a novel degree, will constitute an equivalent to the preferred embodiments. Some such substituted salicylate compounds are disclosed in EP 0 336 812, the disclosure of which is herein incorporated by reference thereto. In some other analogs the 2-position hydroxyl, or both the hydroxyl and the carboxyl groups can be carried on a small hydrocarbon moiety, preferably a substituted methyl, having up to six carbon atoms. An example of such an analog is mandelic acid, $C_6H_5.CH(OH).COOH$.

The most preferred salicylic acid compounds for use in the practice of the present invention embody only minor changes in the structure of the base salicylic acid molecule, such for example as the inclusion of no more than three additional carbon atoms of a homopolar character, such as the substitution of methyl, ethyl or propyl in the 3, 4 or 5 position.

In the best embodiment known to applicant, the salicylic acid is unsubstituted salicylic acid itself, while another preferred such acid is methyl salicylic acid. Being of a more irritant nature to some people, methyl salicylic acid is preferably included as a mixture with salicylic acid. Some other salicylic acids, within the meaning of the present invention are: 2-hydroxy-4-(or -5-)ethyl benzoic acid, 2-hydroxy-4-(or-5)isopropyl benzoic acid and 2-hydroxy-4-hydroxymethyl-5-n-butyl benzoic acid. Mixtures of salicylic acids can also be used. The salicylic acid used is preferably sufficiently soluble in a somewhat polar hydroalcoholic vehicle to provide an effective solution of active ingredient. In general, salicylic acid is more water-soluble at a neutral pH but more active at the acidic ph's described herein. Notwithstanding its limited water solubility, the lower pH's are preferred for better beneficial activity.

Active ingredient b): alpha hydroxy aliphatic acid

These factors should also be considered when choosing an alternative alpha hydroxy acid to lactic acid. Preferably, the alpha hydroxy acid used in my inventive composition is a straight or branched chain aliphatic acid with not more than three substituents in the aliphatic backbone, said substituents being non-basic and being selected from the group consisting of hydroxy, aldehyde, keto, carboxyl, chloro and nitro.

While acidity and water or hydroalcoholic solubility are desirable characteristics of the alphahydroxy acids of the present invention, any extremes of these characteristics, such as would be displayed by a mineral acid, is undesirable as being liable to induce not just irritation but severe clinical conditions such as burning, lesions and sub-cutaneous penetration. Such undesired characteristics can sometimes be displayed by low molecular weight materials which may exhibit unusual and unpredictable, and often harmful, idiosyncratic behavior.

To avoid these possibilities the preferred alpha hydroxy acid of the present irritation contain at least one hydrophobic moiety being a carbon atom having four substantially non-polar bonds for example carbon-carbon or carbon-hydrogen bonds. Such hydrophobicity balances the electronegative radicals for improved biological compatibility and efficiency.

The most preferred alpha hydroxy aliphatic acid for use in the practice of the present invention is lactic acid.

Other alpha hydroxy aliphatic acids to be used should, in general, satisfy the requirements set forth for the particular salicylic acids selected for use in the present invention, as described above.

Such other alpha hydroxy aliphatic acids are preferably monocarboxylic acids selected from the group consisting of 2-hydroxy-n-butanoic acid, 2-hydroxy-isobutanoic, 2-hydroxy-n-pentanoic, 2-hydroxy-isopentanoic, 2-hydroxy-n-hexanoic acid, 2-hydroxy-isohexanoic acid. Di- or polyhydric analogs thereof can also be used, for example, 2,X-dihydroxy analogs thereof where "X" is an integer from 3 to 6, as appropriate for the respective monohydroxy acid, indicating the carbon atom location of a second hydroxyl substituent in a carbon atom other than the one or two carbon atoms. Preferably, such dihydroxy acids balance the additional electronegativity attributable to the second hydroxyl with a further hydrophobic moiety as described above. Some examples of suitable dihydroxy acids are maleic acid, $(CH.COOH)_2$ and azelaic acid $HOOC.(CH_2)_7.COOH$.

Proportion of salicylic to alpha hydroxy acid

My data have shown a surprising criticality in the relative proportions of salicylic acid and alpha hydroxy acid at a ratio of approximately 1:2 parts by weight. Based on the data described below, there is clearly a novel synergistic effect taking place at relative proportions of about 1:2 parts by weight, say from about 1:1.7 to 1:2.3 parts by weight. This synergistic effect shows a peak combination of high cell renewal activity coupled with a low irritation level, as shown in clinical studies. The advantages of this phenomenon can of course be obtained within a broader range of proportions, the precise limits and mathematical characterization of which can be demonstrated by further experimentation beyond that reported here. However, it appears that such advantages are obtainable within a range of proportions of the salicylic acid to alpha hydroxy carboxylic acid of from about 1:1.0 to 1:4.0, or preferably, from about 1:1.5 to 1:3.0.

pH of composition

An important characteristic of the skin-conditioning composition of this invention is that it have substantial acidity and be capable of promoting a substantially acidic environment when applied to the skin. My test data show that a particularly desirable combination of properties, namely high cell renewal efficacy and a low irritation is displayed by a skin-conditioning composition having a pH near 5, for example from about 4.0 to 5.5, preferably a pH of from about 4.8 to 5.2. This effect is quite pronounced when the proportion of salicylic acid to alpha hydroxy acid is close to 1.0:2.0. At lower pH levels, good activity is demonstrated within a somewhat wider range of proportions of acids, namely of from about 1.5 to 2.0 parts of alpha hydroxy acid per part of salicylic acid.

At such lower pH levels, cell turnover is nearly as efficient, but the irritation factor increases. Such irritation levels become unattractive or unacceptable for over-the-counter skin-conditioning compositions, but are appropriate for professional use by beauticians or dermatologists. For such professional use the pH range can be from about 2.5 to 4.5.

One preferred skin-conditioning composition according to my invention is formulated as a non-prescription over-the-counter composition comprising from about 0.15 to 9 percent, preferably from about 2.5 to 7.5 percent, of said salicylic acid together with said alpha hydroxy carboxylic acid and having a pH of from about 4.0 to 5.5.

Another preferred skin-conditioning composition according to my invention is formulated for professional use and comprises from about 7.5 to 30 weight percent of said salicylic acid and said carboxylic acid together, and has a pH of from about 2.5 to 4.5. A preferred such professional composition comprises from about 2.5 to 7.5 weight percent of salicylic acid and from about 5.0 to 15.0 weight percent of lactic acid in a proportion of about 1:2.

In general, preferred pH ranges lie in the range of from 3.0 to 6.0. Effective compositions employing a hydroalcoholic vehicle or carrier for the active acids can be formulated with a pH of from 3.0 to 4.5, with pH 3.0 to 3.5 being commercially attractive. Emulsions, for example creams and lotions, can be formulated with a higher pH, for example in the range of from 3.0 to 6.0.

Incorporation of anti-irritants

A further feature of my invention is the discovery that certain materials are effective anti-irritants when incorporated in the novel skin-conditioning compositions described herein and, surprisingly, are capable of effecting a marked reduction in the irritation induced by application of skin-conditioning compositions according to my invention. Preferably, such anti-irritants comprise from about 0.1 to 20 weight percent, more preferably to 10 weight percent, of the skin-conditioning composition and are selected from the group consisting of antioxidants and anti-inflammatory agents.

Some suitable anti-oxidants can be selected from the group consisting of vitamin C, vitamin E, nor-diguaritic acid (NDGA), butylated hydroxyanisole (BHA), butylated hydroxytoluene (BHT), pantetheine, beta-carotene, propyl gallate, rosmarinic acid, superoxide dismutase and catalase, or mixtures thereof. BHT, BHA, propyl gallate, NDGA and rosmarinic acid are generally used in rather small proportions, of less than one weight percent, while vitamins C and E, and the enzymes are used in somewhat greater proportions, for example about 1 to 5 weight percent. Some examples of anti-oxidant formulations that can be used with advantage to enhance the skin-conditioning compositions of this invention with approximate percentages by weight of skin-conditioning composition, are:

0.3% BHT, 2% vitamin E, 0.1% vitamin C with 0.1% propyl gallate;

1% catalase with 2% superoxide dismutase;

5% vitamin C;

0.3% BHT with 0.1% NDGA; and 0.3% BHT with 0.1% rosmarinic acid.

Some suitable anti-inflammatory agents can be selected from the group consisting of caffeine, theophylline, hydrocortisone, cola nut extract and green tea extract, or mixtures thereof. These agents are preferably used in proportions of about 0.5 to 5.0 weight percent, with the natural extracts being used at the higher end of this range. Some examples of anti-inflammatory formulations that can be used with advantage to enhance the skin-conditioning compositions of this invention, with approximate percentages by weight of skin-conditioning composition, are:

5% cola nut, rosemary or green tea extract;

0.5 to 2% hydrocortisone;

1.0% caffeine;

0.2% caffeine with 2.0% theophylline;

1.0% alpha-bisabolol; and 5.0% aloe.

Hydroalcoholic vehicle

The active ingredients can be formulated in a cosmetically acceptable hydroalcoholic vehicle having from about 40 to 75 weight percent of water, preferably 55 to 65 or about 60%, and from about 25 to 55 weight percent, preferably from about 25 to 35 or about 30 percent of an aliphatic alcohol. While a number of lower aliphatic alcohols, both monohydric and polyhydric can be used, ethanol and propanol are the most preferred choices. Many additives and supplemental materials are known to the art as being useful for incorporation in such vehicles, for example, glycerine up to about 5 percent, preferably 1 or 2 percent is useful as a humectant to counteract the drying effect of the alcohol and to improve the feel of the tonic. Stabilizers, fragrances and colorants are examples of other such additives.

If necessary, pH adjustment to an acceptable range can be effected with from 0.1 to 10 weight percent of an alkaline medium, for example aqueous sodium hydroxide, arginine or triethanolamine (TEA). Since the pH of the skin-conditioning compositions of this invention has an important bearing on their efficacy, the presence of an appropriate buffer may also be desirable. Any such buffer or buffering system, acting in conjunction with said alkaline medium, should of course act to provide an acidic pH within the ranges described above, and preferably to keep the pH at 4.5 or below. The quantity of buffer will depend upon its strength but will usually be from about 0.1 to 10 weight percent, preferably about 1 or 2 percent. Some suitable buffers are TRIS (trimethylolaminomethane) buffers and phosphate buffers.

EXAMPLE 1

Preparation of a Skin-conditioning Cream

Stage 1

The following ingredients, in proportions based on the weight of the end-product cream, are mixed and heated to 75° C., with agitation, until the phase clears:

| lanolin 2060 | 2.0 |
|---|---|
| Promulgen D | 2.5 |
| (trade mark of Amerchol Corp.) | |
| cetearyl alcohol and ceteareth-20 | |
| glyceryl monostearate | 2.0 |
| mineral oil, light grade | 8.5 |
| lanolin alcohol | 1.0 |
| sesame oil | 1.0 |
| squalane | 2.0 |
| propyl paraben | 0.1 |
| PEG-100 stearate | 0.75 |
| (polyethylene glycol stearate averaging 100 monomer groups per molecule) | |
| | 19.85 |

Stage 2

The following ingredients are mixed together, separately from the Stage 1 ingredients, and heated to 75° C. with agitation until the phase clears:

| deionized water | 50.60 |
|---|---|
| 1,3-butylene glycol | 4.25 |
| methyl paraben | 0.25 |
| salicylic acid | 1.00 |
| | 56.10 |

Stage 1 and Stage 2 ingredients are combined with vigorous agitation in a blender until a smooth, continuous emulsion forms.

Stage 3

The following ingredients are mixed at 45° C.:

| deionized water | 5.0 |
|---|---|
| imidazolidinyl urea | 0.25 |
| | 5.25 |

The smooth, hot, combined emulsion from Stage 2 is cooled to 45° C. with continuous mixing and the above mix of water/urea ingredients is slowly added to the cooled Stage 2 emulsion, while continuing to mix.

Stage 4

The following ingredients are mixed at 45° C. and added to the emulsion from Stage 3, with continuous mixing:

| lactic acid | 2.0 |
|---|---|
| deionized water | 3.375 |
| | 5.375 |

Stage 5

The following ingredients are mixed at 45° C. and added to the emulsion from Stage 3, with continuous mixing:

| anti-oxidant (aqueous 1% catalase with 2% superoxide dismutase) | 5.0 |
|---|---|

Mixing is continued until the surface of the emulsion is smooth and shiny. Then sodium hydroxide is added to adjust the pH to 4.5 to 4.7. When the pH is in range, sufficient water is added to bring the ingredient total to 100.00. Then, the emulsion is cooled to room temperature, with continued agitation, whereupon it is ready for packaging or storage, prior to use.

The manufacturing approach used in this example is generally applicable to the formulation of a wide range of cosmetic materials with the skin-conditioning properties of this invention, by dissolving the appropriate salicylic and alpha hydroxy acids in suitable, cosmetically acceptable or compatible solvents and admixing the resultant solution or solutions with conventional cosmetic ingredients, employing the optional ingredients of the invention, such as buffers and anti-irritants, as desired by the formulator or customer.

SKIN-CONDITIONING EFFICACY TESTING

A simple cell renewal assay was used to determine the effectiveness of various combinations of salicylic and lactic acid in improving skin condition. The ability to promote cell renewal has been found to be an effective marker indicating, or associated with, what are known as anti-aging benefits including, firming of the skin, increasing skin thickness and reducing the appearance of lines and wrinkles.

PROCEDURES

Cell renewal increase %

Twenty panelists are patched with 5% dansyl chloride, a fluorescent stain, in petrolatum, on four test sites, two on each volar forearm. The subjects are examined on day 1 to ensure the stain has taken. Using three sites on each panelist and leaving the fourth as a control, test samples are applied with Q-tips, to randomized sites. The panelists are examined at intervals, commencing at day 7, using a quartz mineral light to detect the presence of residual stain at the test sites, examination continuing until the stain is removed.

Additionally, on day 0 and at the end of the study, all test sites, including the controls, are gently scrubbed with a detergent solution to remove loosely adhering squames which are then quantified as cell renewal increase %, using known cell counting techniques.

Irritation

Irritation was evaluated by comparative chromaticity determinations of skin color, by industry standard methods, employing a Minolta Chroma Meter, Minolta Camera Co. Ltd. Additional subjective perceptions of stinging, burning and skin redness after application were recorded, and the data were combined into a clinical irritation index having a scale of from 0 to 5 on which 0 indicates no discernible or reported irritation, and 5 indicates severe irritation.

Test samples, in the following tests, comprise aliquots of skin-conditioning cream compositions equivalent to that set forth in Example 1 employing the preferred active ingredients, lactic and salicylic acid, with variations of proportions or conditions as shown in the test results below.

Test A: Varying proportions of salicylic acid to lactic acid.

| SA:LA | PH | Cell Renewal Increase % | Clinical Irritation | Activity Index |
|---|---|---|---|---|
| 3.0:0.0 | 5 | 19 | 2.4 | 7.9 |
| 2.5:0.5 | 5 | 18 | 2.2 | 8.2 |
| 2.0:1.0 | 5 | 15 | 2.0 | 7.5 |
| 1.5:1.5 | 5 | 17 | 1.9 | 8.9 |
| 1.0:2.0 | 5 | 34 | 1.6 | 21.2 |
| 0.5:2.5 | 5 | 21 | 2.0 | 10.5 |
| 0.0:3.0 | 5 | 17 | 1.9 | 8.9 |

"SA:LA" is the ratio of salicylic acid to lactic acid.
"Activity Index" is (Cell Renewal Increase %)/(Clinical Irritation)

In Test A, the pH is held constant at 5, while the ratio of salicylic acid to lactic acid is varied through a wide range. The results show a pronounced synergistic effect, with a sharp peak in efficacy, as measured by cell renewal increase percentage, at a proportion of 1.0:2.0, coupled with a dip in the important side effect, irritation at the same proportion. The activity index which is proportional to cell renewal increase % and inversely proportional to clinical irritation further illustrates the synergism at and around a ratio of 1.0:2.0 salicylic acid to lactic acid.

Test B: Varying pH conditions

| SA:LA | PH | Cell Renewal Increase % | Clinical Irritation | Activity Index |
|---|---|---|---|---|
| 1.0:2.0 | 3 | 37 | 2.7 | 13.7 |
| 1.0:2.0 | 4 | 35 | 2.4 | 14.6 |
| 1.0:2.0 | 5 | 34 | 1.6 | 21.2 |
| 1.0:2.0 | 6 | 21 | 1.1 | 19.1 |
| 1.0:2.0 | 7 | 14 | 1.1 | 12.7 |
| 1.0:2.0 | 8 | 11 | 1.2 | 9.2 |

In test B, the ratio of salicylic acid to lactic acid is held constant while the pH is varied from a very acid pH 3 to a slightly alkaline pH 8. Both the efficacy, as measured by cell renewal rates, and the irritation level increase with increasing pH. However, the cell renewal rate only increases slowly below pH 5, while the irritation rate rises more sharply. The higher irritation rates below pH 5 suggest such compositions are more suitable for use under professional supervision. This conclusion is confirmed by the activity index which shows a peak at a pH of 5 and declines rapidly at lower pH's in view of the higher irritation levels.

Test C: Varying the combined quantity of salicylic and lactic acid, as a percentage of the composition at a constant pH of 5 and a proportion of 1:2.

| Quantity of salicylic acid and lactic acid combined | Cell Renewal Increase % | Clinical Irritation | Activity Index |
|---|---|---|---|
| 0.3 | 16 | 0.6 | 26.7 |
| 0.6 | 19 | | |
| 0.9 | 18 | | |
| 1.5 | 21 | | |
| 3.0 | 34 | 1.6 | 21.2 |
| 4.5 | 37 | | |
| 6.0 | 39 | | |
| 9.0 | 45 | 2.7 | 16.7 |
| 12.0 | 46 | 3.2 | 14.4 |

Test C shows that both efficacy and side effects increase with an increase in the combined quantities of active ingredients. A quantity of 3.0 percent shows an excellent balance of high efficacy and low side effects. Below 3.0, some useful efficacy is still displayed, and the irritation level is attractively low. Above about 9 weight percent there is little improvement in efficacy, while the irritation level continues to increase. Accordingly, such proportions become less attractive. Here, the activity index is unduly influenced by a very low irritation level: addition of a time-related factor could improve this index.

Test D (Comparative): Varying proportions of salicylic acid to glycolic acid.

| SA:GA | PH | Cell Renewal Increase % | Clinical Irritation | Activity Index |
|---|---|---|---|---|
| 3.0:0.0 | 5 | 22 | 2.2 | 10.0 |
| 2.0:1.0 | 5 | 21 | 2.4 | 8.8 |
| 1.5:1.5 | 5 | 22 | 2.5 | 8.8 |
| 1.0:2.0 | 5 | 17 | 2.2 | 7.7 |
| 0.0:3.0 | 5 | 16 | 2.1 | 7.6 |

"SA:GA" is the ratio of salicylic acid to glycolic acid.

"SA:GA" is the ratio of salicylic acid to glycolic acid. Increasing proportions of glycolic acid somewhat reduce the efficacy of salicylic acid, as shown by cell renewal increase rates, with no significant peaks in cell renewal increase or dips in clinical irritation. Moreover, the cell renewal rates are substantially lower than those obtained with salicylic and lactic acids combined, under preferred conditions. Furthermore, the cell renewal increase levels, reading down the column of respective acid proportions, show that the activity level for glycolic acid alone or as a major component, is less than that of salicylic acid. Still further, the irritation level induced by glycolic acid is substantially higher than provided by preferred combinations of salicylic and lactic acid. The activity index shows a slow decline with rising pH and an overall much lower level than is obtained with the inventive compositions.

Clearly, a combination of salicylic acid with glycolic acid does not produce the desirable effects attributable to a combination of salicylic and lactic acids.

Test E (Comparative)

Varying Proportions of Salicylic Acid to Glycolic Acid at pH 3 and 4

To examine further the efficacy of combinations of glycolic acid with salicylic acid, additional tests were conducted at lower pH levels, with the following results:

| Ratio of salicylic acid to glycolic acid | PH | Cell Renewal Increase % |
|---|---|---|
| 3.0:0.0 | 3 | 25 |
| 2.5:0.5 | 3 | 24 |
| 1.5:1.5 | 3 | 25 |
| 0.0:3.0 | 3 | 17 |
| 3.0:0.0 | 4 | 22 |
| 1.5:1.5 | 4 | 25 |
| 0.0:3.0 | 4 | 16 |

Little, if any, improvement in cell renewal increase was obtained at the lower pH levels, further confirming the lack of the synergistic effect shown by lactic and salicylic acid. While irritation data was not obtained in this particular case, (clinical studies being expensive) as Test B shows and common sense suggests, irritation levels can be expected to be substantially higher at the lower pH levels.

Test F: Salicylic acid with other acids in a proportion of 1.0:2.0

| Other Acid | PH | Cell Renewal Increase % | Clinical Irritation | Activity Index |
|---|---|---|---|---|
| Lactic | 5 | 34 | 1.6 | 21.2 |
| Glycolic | 5 | 17 | 2.2 | 7.7 |
| Citric | 5 | 14 | 1.9 | 7.4 |
| Pyruvic | 5 | 20 | 2.4 | 8.3 |
| Mandelic | 5 | 20 | 2.4 | 8.3 |
| Maleic | 5 | 22 | 2.5 | 8.8 |
| Azelaic | 5 | 24 | 1.7 | 14.1 |
| Azelaic | 4 | 29 | 2.9 | 10.0 |
| Lactic | 4 | 35 | 2.4 | 14.6 |

The data for lactic and glycolic acids are repeated from previous tests for comparative purposes. Clearly, none of these acids when used in combination with salicylic acid at preferred proportions and pH levels, is as effective as a combination of lactic acid with salicylic acid. However, referring to the activity indexes, it can be seen that azelaic acid is better than glycolic acid, showing somewhat better activity and reduced irritation.

EXAMPLE 3

Skin-conditioning Composition with an Antioxidant

The following ingredients, in the proportions indicated are blended until a clear solution is obtained, to provide a control in which an anti-oxidant is absent:

| | |
|---|---|
| deionized water | about 60.3 |
| SD alcohol 40 | 35 |
| salicylic acid | 1.0 |
| lactic acid | 2.0 |
| glycerine | 1.5 |
| TEA sufficient to give the pH indicated in the following test. | |

The amount of TEA, and consequently of water, was varied to give different pH levels, as shown below. A solution containing antioxidant was prepared by replacing 3.3 parts of deionized water with the following:

| | |
|---|---|
| catalase | 1.0 |
| superoxide dismutase | 2.0 |
| BHT | 0.3 |

These solutions were used in the following test, Test G.

Test G: Effect of the inclusion of an anti-oxidant at various pH levels

| Ratio of salicylic acid to lactic acid | PH | Anti-oxidant: Absent (−) Present (+) | Clinical Irritation |
|---|---|---|---|
| 1.0:2.0 | 3 | − | 3.0 |
| 1.0:2.0 | 3 | + | 2.0 |
| 1.0:2.0 | 4 | − | 2.8 |
| 1.0:2.0 | 4 | + | 1.7 |
| 1.0:2.0 | 5 | − | 2.4 |
| 1.0:2.0 | 5 | + | 1.6 |

Test subjects were treated for four weeks twice a day with the inventive product of Example 3 at the pH indicated. The data show a substantial and significant reduction in irritation as compared with the data from Test A 1 attributable to the presence of an anti-oxidant in the composition.

These test results, showing improved balances of increases in cell renewal rates and modest irritation levels obtainable with compositions according to the present invention, suggest that such compositions will provide anti-aging benefits, including skin firming, increase of skin thickness, and a reduction of the appearance of lines and wrinkles.

EXAMPLE 2

Preparation of a Skin-conditioning Cream Using an Alternative Formulation

Stage 1

The following ingredients, in proportions based on the weight of the end-product cream, are mixed and heated to 70° C., with agitation, until the phase clears:

| | |
|---|---|
| sesame oil | 8.3 |
| BHT | 0.3 |
| vitamin E | 2.0 |
| glyceryl stearate | 3.0 |
| white petrolatum | 0.5 |
| stearic acid | 3.0 |
| Bernel ester 168 (Bernel Chem. Co. Engelwood NJ) | 3.0 |
| propyl paraben | 0.05 |
| 1,3 butylene glycol | 2.0 |

Stage 2

The following ingredients are mixed together, separately from the Stage 1 ingredients, and heated to 70° C. with agitation until the phase clears:

| | |
|---|---|
| deionized water | 61.51 |
| lactic acid | 2.0 |
| trisodium EDTA | 0.15 |
| methyl paraben | 0.28 |
| imidazolidinyl urea | 0.3 |
| butyl paraben | 0.3 |
| catalase | 1.0 |
| superoxide dismutase | 2.0 |

| | |
|---|---|
| kola nut extract | 5.0 |

Stage 1 and Stage 2 ingredients are combined with vigorous agitation in a blender, with side wiping, until a smooth, continuous emulsion forms. Product inversion may occur.

Stage 3

The following ingredients are mixed at 70° C.:

| | |
|---|---|
| deionized water | 3.0 |
| salicylic acid | 1.0 |
| TEA 99 | 1.25 |
| water to 100 parts | | ensuring that neutralized salicylic acid is fully dissolved. This solution is added to the emulsion of Stage 2, while still hot, and mixing is continued for 30 minutes. The product is silversened and the emulsion cooled slowly to 45° C. with side-wiping, then slowly cooled to room temperature.

The skin-conditioning cream produced by the method of Example 2 is suitable for marketing as an over-the-counter product for direct application to the skin, by consumers, with benefits similar to those demonstrated for Example 1.

The smooth, hot, combined emulsion from Stage 2 is cooled to 45° C. with continuous mixing and the above mix of water/urea ingredients is slowly added to the cooled Stage 2 emulsion, while continuing to mix.

Stage 4

The following ingredients are mixed at 45° C. and added to the emulsion from Stage 3, with continuous mixing:

| | |
|---|---|
| lactic acid | 2.0 |
| deionized water | 3.375 |
| | 5.375 |

Stage 5

The following ingredients are mixed at 45° C. and added to the emulsion from Stage 3, with continuous mixing:

| | |
|---|---|
| anti-oxidant | 5.0 |
| (aqueous 1% catalase with 2% superoxide dismutase) | |

Mixing is continued until the surface of the emulsion is smooth and shiny. Then sodium hydroxide is added to adjust the pH to 4.5 to 4.7. When the pH is in range, sufficient water is added to bring the ingredient total to 100.00. Then, the emulsion is cooled to room temperature, with continued agitation, whereupon it is ready for packaging or storage, prior to use.

Test H

Effect of the Inventive Composition in Reducing Hair Loss and Stimulating Hair Growth-related Conditions To determine potential activity of the compositions of the invention in preventing or reducing hair loss, and in encouraging hair growth, test subjects with moderate to severe hair loss were treated with a scalp tonic comprising the preferred hydroalcoholic vehicle described above to which were added salicylic acid and lactic acid in the proportions set forth below. A placebo was used as one control and data without treatment provided another. Treatments were effected by topical application of the tonic twice a day for three months.

Hair loss was assessed via a combing technique and by measuring the anagen-to-telogen ratios of plucked hairs. These ratios are regarded as reliable indicators of hair growth. Hair goes through several phases of which anagen is an actively growing phase while telogen is a dormant phase.

Combing tests were conducted twice weekly. Subjects in groups of ten were shampooed and rinsed using a sink filter to collect any fallen hairs. Subsequently, each subject's hair was combed 100 times to remove loose hairs which were collected, combined with the subject's washed out hairs, counted and recorded. This procedure was repeated prior to treatment and while using the scalp tonic described above.

The following results were obtained:

| Ratio of salicylic acid to lactic acid | PH | Anagen/Telogen Ratio | Hair Collected |
|---|---|---|---|
| No treatment | | 0.12 | 100 |
| Placebo vehicle | | 0.19 | 95 |
| 1.0:2.0 | 5 | 0.33 | 62 |
| 3.0:0.0 | 5 | 0.21 | 88 |
| 0.0:3.0 | 5 | 0.20 | 86 |

The above results show a significant improvement, of about sixty percent, in anagen/telogen ratios as a result of treatment with a salicylic-lactic acid combination, in accordance with the invention. Here the vehicle shows some effect, while the acids alone show little if any significant effect. A significant reduction of collected hairs was found with the inventive composition. The individual acids show some reduction, but the combination shows a much more pronounced reduction of hair loss.

Addition of an antioxidant to the inventive composition did not reduce product efficacy, however it did decrease perceived irritation which in some cases was reported as a tingling or tightness of the test area, or itchiness.

Dosages and Regimens

Typical application rates of the inventive skin-conditioning compositions described herein can range from about 0.01 to 0.5 mg of active acid ingredients per square centimeter of skin, with 0.05 to 0.2 mg/cm$^2$ being preferred. Cosmetic creams are generally applied at a rate of about 2–3 mg/cm$^2$. With an active ingredient proportion of about 0.15 to about 30 weight percent, this gives a possible rate of application of active ingredients of from about 0.003 mg/cm$^2$ to 0.9 mg/cm$^2$. A preferred range is from about 0.01 to 0.5 mg/cm$^2$, with a range of from 0.05 to 0.2 mg/cm$^2$ active ingredient per unit skin area being more preferred. Using a preferred proportion of about 3% active acidic ingredients, in total, gives a preferred application rate of 0.06 to 0.09 mg/cm$^2$.

This dosage is applied to whatever skin area requires treatment, preferably twice a day. More frequent applications of three or four times a day are likely to be wasteful of product without providing additional benefits, whereas less frequent applications, notably once a day, result in reduced efficacy. Additional applications may occasionally be made after washing, bathing or swimming, up to a maximum of about six times a day.

One individual may use both a lower strength nonprescription or consumer preparation and a higher strength professional preparation intended for use under the supervision of dermatological professionals. The consumer preparation is used on any desired area, including the face, while the professional preparation can be applied to spot defects. The consumer composition can be helpful in alleviating problems of wrinkles, sun damage and cracking with some effect on age spots, while the professional composition can be more effective on age spots, keratoses and other more serious skin problems.

One preferred regimen comprises a regular program of twice daily treatments for an indefinite period employing the consumer composition, employing the more preferred ingredients and proportions of the invention, as set forth above. Such preferred compositions desirably have a proportion of salicylic acid to lactic acid close to 1.0:2.0, a total proportion of active ingredients of about 3% and a pH close to 5. Such a continual regimen is preferably accompanied by dermatological clinic visits to monitor progress. While a high initial dose to obtain prompt improvement could be used, such may elicit a high initial irritation rate. These above-described dosages are generally appropriate for the application of a skin-conditioning cream to most exposed or exposable skin surfaces, but such would generally not be appropriate for application to the scalp.

In applying a non-creamy, hydroalcoholic-based scalp tonic somewhat lower application rates than for skin creams are used. About 3 to 10 ml. containing about 1 mg. per ml. of active acidic ingredients, are usually sufficient to cover a whole scalp, typically about 100 to 200 $cm^2$, giving an application rate of about 0.03 to 0.05 $mg/cm^2$, assuming the larger applications are applied to the larger scalp areas.

A preferred procedure is to apply a scalp treatment, for example the tonic, twice a day, morning and night, by rubbing into the scalp with a cotton ball or equivalent.

Preliminary data suggests that the efficacy of minoxidil, a well-known antialopecia agent, or hair-loss prevention agent, is enhanced by combination with the inventive two-component acid system described herein. Thus minoxidil, in conventional proportions as known to the art, such for example as from 0.5 to 5.0 percent by weight of the composition, can be included in any of the inventive compositions described herein. The use of minoxidil in combination with a salicylic acid derivative is disclosed in EP 0 336 812, the disclosure of which is herein incorporated by reference thereto. This European publication also discloses a family of minoxidil analogs which can also be incorporated in the compositions of the present invention, in the manner described above for minoxidil.

Test I: Effect of Water Solubility on the Therapeutic Index of Various Acid Combinations

| | Acid Composition | Therapeutic Index | Water Solubility | Duration of skin pH changes (hr) |
|---|---|---|---|---|
| a) | 2% LA + 1% GA | 11.8 | very | 2–3 |
| b) | 2% LA + 1% SA | 17.6 | little | 6 |
| c) | 2% LA + 1% mandelic | 16.2 | little | 4–5 |
| d) | 2% LA + 1% (±)tartaric | 16.1 | little | 3–4 |
| e) | 2% LA + 1% (+)tartaric | 11.6 | very | 2 |
| f) | 2% LA + 1% succinic | 16.2 | little | 3–4 |
| g) | 2% LA + 1% isononanoic | 14.6 | little | 3 |
| h) | 3% LA | 11.2 | very | 2–3 |
| i) | 3% GA | 10.6 | very | 1–2 |

Note: "GA" = glycolic acid; "LA" = lactic acid; "SA" = salicylic acid.

Tests were performed on volunteer subjects using the procedures, conditions and ingredients substantially as described in connection with Test F above, while employing the proportion of active acidic ingredients indicated. The therapeutic index is similar to the activity index used in Tables A–F and is a comparative measure of cell renewal increase in relation to irritation induced.

Referring to Test I, it can be seen that samples a) glycolic acid, e) (+)tartaric, natural tartaric or dextrotartaric acid, h) lactic acid alone, and i) glycolic acid alone, are acids which are all readily water soluble and all yield only moderate therapeutic indices, even when used in combination with lactic acid, with a duration of impact on skin pH changes not exceeding 3 hours.

In contrast, samples b) salicylic acid, c) mandelic acid, d) racemic tartaric acid and f) succinic acid are all rather sparingly water soluble, with a solubility less than about 1 g. in 5 ml. of water. When used in combination with lactic acid, as reported in Test I, they yield excellent therapeutic indices in excess of 14.

Of particular note in Test I are the comparative data with the different optically active forms of tartaric acid, which unusually, also have different water solubilities. Thus, (+)tartaric acid is very water soluble, while (±)tartaric acid has only poor water solubility about 14 g./100 ml. This water solubility difference is associated with a significant difference in therapeutic index, sample d) employing the racemic mixture yielding a much higher value of 16.2 versus 11.6 for sample e) employing the individual (+) isomer.

Also of note is that higher therapeutic index values correlate with a longer duration of skin pH changes of from 3–4 hours, and higher, as compared to 2 hours for dextrotartaric acid. These results are consistent with the concept that the therapeutic effects of lactic acid exfoliating compositions can be enhanced by incorporating a moderately water soluble, low molecular weight organic hydroxy acid to prolong skin pH changes. Without being bound by theory, it may be postulated that the presence of lactic acid provides an initial burst of skin pH lowering activity which is continued by the less water soluble acid, low irritant skin cell renewal benefits being attributable to a prolonged lowering of skin pH without excessive irritation, in other words, better control of the skin pH with time. It may further be postulated that previously known more irritant exfoliant compositions associate undesirable or unacceptable irritancy with an excessive lowering of skin pH, albeit for a short time.

While an illustrative embodiment of the invention has been described above, various modifications will be apparent to those of ordinary skill in the art. Such modifications are within the spirit and scope of the invention, which is limited and defined only by the appended claims.

I claim:

1. A low-irritant, skin—cell-renewal-stimulating, cosmetic composition for topical application to normal skin on a daily basis to reduce irregularities of normal skin attributable to aging, said skin—cell-renewal-stimulating cosmetic composition having an acidic pH of from about 4.0 to about 6.0 and comprising from about 0.15 to about 9 percent by weight of acidic cosmetically active ingredients consisting essentially of:

a) salicylic acid; and
b) lactic acid;

dissolved in a cosmetically compatible solvent system in a proportion by weight of from about 1:1.7 to about 1:2.3 salicylic acid to lactic acid.

2. A skin-conditioning, cosmetic composition according to claim 1 providing a skin-cell renewal increase of at least 20% in a skin-stain-removal test, as defined herein, said composition inducing irritation less than 2.0 as defined herein during said test.

3. A skin-conditioning, cosmetic composition according to claim 2 having an activity index in excess of 10 during said test, as defined herein.

4. A skin-conditioning, cosmetic composition according to claim 1 having a pH of from about 4.8 to 5.2.

5. A skin-conditioning, cosmetic composition according to claim 1, for prolonged daily use on normal skin, further comprising from about 0.1 to 20 weight percent of an anti-irritant active ingredient selected from the group consisting of antioxidants and anti-inflammatory agents.

6. A skin-conditioning, cosmetic composition according to claim 1 formulated as a tonic wherein said solvent system comprises a hydroalcoholic vehicle having from about 40 to 75 weight percent of water and from about 25 to 55 weight percent of an aliphatic alcohol.

7. A skin-conditioning composition according to claim 1 for treating dry skin formulated as a cream or lotion with an emollient and a moisturizer, and optionally including a fragrance.

8. A skin-conditioning, cosmetic composition according to claim 1, being a cream, lotion or tonic and further comprising non-acidic, non-pH-reducing, cosmetic additives.

9. A composition according to claim 1, effective as an anti-alopecia agent and further comprising from 0.5 to 5.0 weight percent of minoxidil.

* * * * *